(12) United States Patent
Markham et al.

(10) Patent No.: US 9,814,891 B2
(45) Date of Patent: Nov. 14, 2017

(54) FEEDTHROUGH WITH INTEGRATED BRAZELESS FERRULE

(71) Applicant: HERAEUS DEUTSCHLAND GMBH & CO. KG, Hanau (DE)

(72) Inventors: Jacob Markham, Vadnais Heights, MN (US); Ulrich Hausch, Frankfurt (DE)

(73) Assignee: HERAEUS DUETSCHLAND GMBH & CO. KG, Hanau (DE)

( * ) Notice: Subject to any disclaimer, the term of this patent is extended or adjusted under 35 U.S.C. 154(b) by 0 days.

(21) Appl. No.: 15/225,321

(22) Filed: Aug. 1, 2016

(65) Prior Publication Data

US 2016/0331979 A1 Nov. 17, 2016

Related U.S. Application Data

(62) Division of application No. 13/961,421, filed on Aug. 7, 2013, now Pat. No. 9,403,023.

(51) Int. Cl.
*A61N 1/375* (2006.01)
*C23C 24/08* (2006.01)
*C23C 4/134* (2016.01)

(52) U.S. Cl.
CPC ............ *A61N 1/3754* (2013.01); *C23C 4/134* (2016.01); *C23C 24/087* (2013.01)

(58) Field of Classification Search
CPC .............................. A61N 1/3754; C23C 4/134
USPC ........................................................ 439/884
See application file for complete search history.

(56) References Cited

U.S. PATENT DOCUMENTS

| | | | |
|---|---|---|---|
| 3,648,355 A | * | 3/1972 | Shida .................. B32B 15/018 228/187 |
| 3,979,187 A | | 9/1976 | Scherer |
| 4,152,540 A | | 5/1979 | Duncan et al. |
| 4,217,137 A | | 8/1980 | Kraska et al. |
| 4,315,054 A | | 2/1982 | Sack et al. |
| 4,352,951 A | | 10/1982 | Kyle |
| 4,354,964 A | | 10/1982 | Hing et al. |

(Continued)

FOREIGN PATENT DOCUMENTS

| | | |
|---|---|---|
| DE | 69729719 | 7/2005 |
| DE | 102006054249 | 5/2008 |

(Continued)

OTHER PUBLICATIONS

Exner, Horst et al., "Laser Joining of Ceramics in Liquid Phase," pp. 1-8 (Nov. 8, 2011).

(Continued)

*Primary Examiner* — Alexander Gilman
(74) *Attorney, Agent, or Firm* — Dicke, Billig & Czaja, PLLC (57) ABSTRACT

One aspect provides a feedthrough device for an implantable medical device. The feedthrough includes a ferrule having a metal that is configured to be welded to a case of the implantable device. An insulator is substantially surrounded by the ferrule and shares an interface therewith, the insulator being a glass or ceramic material. Conductive elements are formed through the insulator providing an electrically conductive path through the insulator. There is no braze, solder, or weld joint at the interface between the ferrule and the insulator and that there is no braze or solder at interfaces between the insulator and the conductive elements.

14 Claims, 7 Drawing Sheets

(56) References Cited

U.S. PATENT DOCUMENTS

| | | | |
|---|---|---|---|
| 4,362,792 A | 12/1982 | Bowsky et al. | |
| 4,456,786 A | 6/1984 | Kyle | |
| 4,488,673 A | 12/1984 | Hopper, Jr. | |
| 4,602,956 A | 7/1986 | Partlow et al. | |
| 4,678,868 A | 7/1987 | Kraska et al. | |
| 4,737,601 A | 4/1988 | Gartzke | |
| 4,774,953 A | 10/1988 | Foote | |
| 4,816,621 A | 3/1989 | Huebner et al. | |
| 4,991,582 A | 2/1991 | Byers et al. | |
| 4,992,910 A | 2/1991 | Evans | |
| 5,043,535 A | 8/1991 | Lin | |
| 5,046,262 A | 9/1991 | Kerbaugh | |
| 5,223,672 A | 6/1993 | Pinneo et al. | |
| 5,245,999 A | 9/1993 | Dahlberg et al. | |
| 5,272,283 A | 12/1993 | Kuzma | |
| 5,333,095 A | 7/1994 | Stevenson et al. | |
| 5,407,119 A | 4/1995 | Churchill et al. | |
| 5,408,066 A | 4/1995 | Trapani et al. | |
| 5,513,793 A | 5/1996 | Malmgren | |
| 5,515,604 A | 5/1996 | Horine et al. | |
| 5,654,106 A | 8/1997 | Purnell et al. | |
| 5,683,435 A | 11/1997 | Truex et al. | |
| 5,738,270 A | 4/1998 | Malmgren | |
| 5,750,926 A | 5/1998 | Schulman et al. | |
| 5,769,874 A | 6/1998 | Dahlberg | |
| 5,782,891 A | 7/1998 | Hassler et al. | |
| 5,796,019 A | 8/1998 | Lupton et al. | |
| 5,821,011 A | 10/1998 | Taylor et al. | |
| 5,851,222 A | 12/1998 | Taylor et al. | |
| 5,855,711 A | 1/1999 | Araki et al. | |
| 5,861,714 A | 1/1999 | Wei et al. | |
| 5,866,851 A | 2/1999 | Taylor et al. | |
| 5,870,272 A | 2/1999 | Seifried et al. | |
| 5,905,627 A | 5/1999 | Brendel et al. | |
| 6,093,476 A | 7/2000 | Horiuchi et al. | |
| 6,232,004 B1 | 5/2001 | Lasater | |
| 6,284,080 B1 | 9/2001 | Haq et al. | |
| 6,414,835 B1 | 7/2002 | Wolf et al. | |
| 6,579,492 B2 | 6/2003 | Wehler | |
| 6,586,675 B1 | 7/2003 | Bealka et al. | |
| 6,643,903 B2 | 11/2003 | Stevenson et al. | |
| 6,660,116 B2 | 12/2003 | Wolf et al. | |
| 6,852,925 B2 * | 2/2005 | Wolf | H01M 2/06 174/50.56 |
| 6,999,818 B2 | 2/2006 | Stevenson et al. | |
| 7,035,076 B1 | 4/2006 | Stevenson | |
| 7,038,900 B2 | 5/2006 | Stevenson et al. | |
| 7,068,491 B1 | 6/2006 | Burdon et al. | |
| 7,107,099 B1 | 9/2006 | O'Phelan et al. | |
| 7,136,273 B2 | 11/2006 | Stevenson et al. | |
| 7,145,076 B2 * | 12/2006 | Knappen | A61N 1/3754 174/50.56 |
| 7,174,219 B2 | 2/2007 | Wahlstrand et al. | |
| 7,174,223 B2 | 2/2007 | Dalton et al. | |
| 7,222,419 B2 | 5/2007 | Horng et al. | |
| 7,260,434 B1 | 8/2007 | Lim et al. | |
| 7,274,963 B2 | 9/2007 | Spadgenske | |
| 7,437,817 B2 | 10/2008 | Zhang et al. | |
| 7,480,988 B2 | 1/2009 | Ok et al. | |
| 7,502,217 B2 | 3/2009 | Zhao et al. | |
| 7,561,917 B2 | 7/2009 | Wegrzyn, III et al. | |
| 7,564,674 B2 | 7/2009 | Frysz et al. | |
| 7,569,452 B2 | 8/2009 | Fu et al. | |
| 7,630,768 B1 | 12/2009 | Coffed et al. | |
| 7,668,597 B2 | 2/2010 | Engmark et al. | |
| 7,706,124 B2 | 4/2010 | Zhao et al. | |
| 7,720,538 B2 | 5/2010 | Janzig et al. | |
| 7,736,191 B1 | 6/2010 | Sochor | |
| 7,742,817 B2 | 6/2010 | Malinowski et al. | |
| 7,747,321 B2 | 6/2010 | Fischbach et al. | |
| 7,761,165 B1 | 7/2010 | He et al. | |
| 7,765,005 B2 | 7/2010 | Stevenson | |
| 7,794,256 B1 | 9/2010 | Sochor | |
| 7,812,691 B1 * | 10/2010 | Fisk | H03H 1/0007 333/182 |
| 7,818,876 B2 | 10/2010 | Suaning | |
| 7,901,761 B1 | 3/2011 | Jiang et al. | |
| 7,930,032 B2 | 4/2011 | Teske et al. | |
| 7,966,070 B2 * | 6/2011 | Taylor | A61N 1/3754 607/36 |
| 7,970,474 B2 | 6/2011 | Starke | |
| 7,989,080 B2 | 8/2011 | Greenberg et al. | |
| 8,000,804 B1 | 8/2011 | Wessendorf et al. | |
| 8,065,009 B2 | 11/2011 | Biggs | |
| 8,131,369 B2 | 3/2012 | Taylor et al. | |
| 8,131,376 B1 | 3/2012 | Faraji et al. | |
| 8,155,743 B2 | 4/2012 | Rundle et al. | |
| 8,163,397 B2 | 4/2012 | Ok et al. | |
| 8,179,658 B2 | 5/2012 | Brendel et al. | |
| 8,189,333 B2 | 5/2012 | Foster | |
| 8,288,654 B2 | 10/2012 | Taylor et al. | |
| 8,346,362 B2 | 1/2013 | Kinney et al. | |
| 8,355,785 B1 | 1/2013 | Hammond et al. | |
| 8,391,983 B2 | 3/2013 | Lim | |
| 8,494,635 B2 | 7/2013 | Troetzschel et al. | |
| 8,497,435 B2 | 7/2013 | Nagata et al. | |
| 8,528,201 B2 | 9/2013 | Troetzschel et al. | |
| 8,552,311 B2 | 10/2013 | Koester et al. | |
| 8,642,887 B1 * | 2/2014 | Li | A61N 1/3754 174/50.6 |
| 8,656,736 B2 | 2/2014 | Terao | |
| 8,659,870 B2 | 2/2014 | Brendel et al. | |
| 8,742,268 B2 | 6/2014 | Reisinger et al. | |
| 8,755,887 B2 | 6/2014 | Troetzschel et al. | |
| 8,825,162 B2 | 9/2014 | Reisinger | |
| 8,886,320 B2 | 11/2014 | Troetzschel et al. | |
| 8,894,914 B2 | 11/2014 | Pavlovic | |
| 8,929,987 B2 | 1/2015 | Troetzschel et al. | |
| 9,048,608 B2 * | 6/2015 | Pavlovic | H01R 43/20 |
| 9,306,318 B2 * | 4/2016 | Reisinger | A61N 1/3754 |
| 9,403,023 B2 | 8/2016 | Markham et al. | |
| 9,431,801 B2 * | 8/2016 | Markham | H02G 1/00 |
| 9,552,899 B2 * | 1/2017 | Specht | A61N 1/3754 |
| 2001/0013756 A1 | 8/2001 | Mori et al. | |
| 2001/0018012 A1 | 8/2001 | Harmand et al. | |
| 2001/0041227 A1 | 11/2001 | Hislop | |
| 2002/0166739 A1 | 11/2002 | Naerheim | |
| 2003/0109903 A1 | 6/2003 | Berrang et al. | |
| 2004/0023101 A1 | 2/2004 | Jacobson et al. | |
| 2004/0116976 A1 | 6/2004 | Spadgenske | |
| 2004/0128016 A1 | 7/2004 | Stewart | |
| 2005/0247475 A1 | 11/2005 | Stevenson et al. | |
| 2006/0025866 A1 | 2/2006 | Serafin, Jr. et al. | |
| 2006/0028784 A1 | 2/2006 | Brendel | |
| 2006/0247714 A1 | 11/2006 | Taylor et al. | |
| 2006/0259093 A1 | 11/2006 | Stevenson et al. | |
| 2007/0041164 A1 | 2/2007 | Greenberg et al. | |
| 2007/0060970 A1 | 3/2007 | Burdon et al. | |
| 2007/0134985 A1 * | 6/2007 | Frysz | H01G 4/232 439/620.09 |
| 2007/0183118 A1 | 8/2007 | Fu et al. | |
| 2007/0217121 A1 | 9/2007 | Fu et al. | |
| 2007/0276389 A1 | 11/2007 | Franke et al. | |
| 2008/0060834 A1 | 3/2008 | Eck et al. | |
| 2008/0071313 A1 | 3/2008 | Stevenson et al. | |
| 2008/0119906 A1 | 5/2008 | Starke | |
| 2008/0203917 A1 | 8/2008 | Maya | |
| 2008/0269831 A1 | 10/2008 | Erickson | |
| 2009/0192578 A1 | 7/2009 | Biggs | |
| 2009/0281586 A1 | 11/2009 | Lim | |
| 2010/0023086 A1 | 1/2010 | Lim | |
| 2010/0109966 A1 | 5/2010 | Mateychuk et al. | |
| 2010/0121438 A1 | 5/2010 | Jarvik | |
| 2010/0241206 A1 | 9/2010 | Truex et al. | |
| 2010/0258342 A1 | 10/2010 | Parker | |
| 2011/0032658 A1 | 2/2011 | Iyer | |
| 2011/0034965 A1 | 2/2011 | Troetzschel et al. | |
| 2011/0034966 A1 | 2/2011 | Troetzschel et al. | |
| 2011/0048770 A1 | 3/2011 | Reiterer et al. | |
| 2011/0094768 A1 | 4/2011 | Davis et al. | |
| 2011/0106228 A1 | 5/2011 | Reiterer et al. | |
| 2011/0186349 A1 * | 8/2011 | Troetzschel | B28B 1/00 174/650 |
| 2011/0190885 A1 | 8/2011 | Troetzschel et al. | |

(56) References Cited

U.S. PATENT DOCUMENTS

| | | |
|---|---|---|
| 2011/0232961 A1 | 9/2011 | Teske |
| 2011/0232962 A1 | 9/2011 | Teske |
| 2011/0303458 A1* | 12/2011 | Sutay ............... H01G 4/35 174/650 |
| 2012/0006576 A1 | 1/2012 | Barry et al. |
| 2012/0127627 A1 | 5/2012 | Brendel et al. |
| 2012/0193117 A1 | 8/2012 | Specht et al. |
| 2012/0193118 A1 | 8/2012 | Kempf et al. |
| 2012/0193119 A1 | 8/2012 | Kempf et al. |
| 2012/0193125 A1 | 8/2012 | Pavlovic et al. |
| 2012/0193141 A1 | 8/2012 | Reisinger et al. |
| 2012/0194981 A1 | 8/2012 | Kempf et al. |
| 2012/0197326 A1 | 8/2012 | Pavlovic |
| 2012/0197327 A1 | 8/2012 | Specht |
| 2012/0197335 A1 | 8/2012 | Reisinger |
| 2012/0197368 A1 | 8/2012 | Reisinger |
| 2012/0200011 A1 | 8/2012 | Pavlovic |
| 2012/0203294 A1* | 8/2012 | Troetzschel ....... H01R 13/5224 607/5 |
| 2013/0035733 A1 | 2/2013 | Breyen et al. |
| 2013/0060312 A1 | 3/2013 | Iyer et al. |
| 2013/0184797 A1 | 7/2013 | Tang et al. |
| 2013/0299233 A1 | 11/2013 | Troetzschel et al. |
| 2014/0008121 A1 | 1/2014 | Troetzschel et al. |
| 2014/0144014 A1 | 5/2014 | Troetzschel et al. |
| 2014/0262494 A1 | 9/2014 | Reisinger et al. |
| 2014/0368298 A1 | 12/2014 | Reisinger |
| 2015/0045860 A1* | 2/2015 | Markham ............ A61N 1/3754 607/116 |

FOREIGN PATENT DOCUMENTS

| | | |
|---|---|---|
| DE | 102008021064 | 10/2009 |
| DE | 102009035971 | 2/2011 |
| DE | 102009035972 | 4/2011 |
| DE | 102010006837 | 8/2011 |
| DE | 102010006838 | 8/2011 |
| DE | 102010006689 | 9/2011 |
| DE | 102010006690 | 9/2011 |
| DE | 102011119125 | 5/2013 |
| EP | 0877400 | 11/1998 |
| EP | 0916364 | 5/1999 |
| EP | 1685874 | 8/2006 |
| EP | 1754511 | 2/2007 |
| EP | 2398026 | 12/2011 |
| WO | 03073450 | 9/2003 |
| WO | 2004110555 | 12/2004 |
| WO | 2008103166 | 8/2008 |
| WO | 2010091435 | 8/2010 |
| WO | 2013075797 | 5/2013 |

OTHER PUBLICATIONS

Hussain, et al., "Electrical conductivity of an insulator matrix (alumina) and conductor particle (molybdenum) composites", Journal of the European Ceramic Society, vol. 23, Issue 2, Feb. 2003, pp. 315-321.

Gil et al., "Grain Growth Kinetics of Pure Titanium," Scripta Metallurgica et Materialia, vol. 33, No. 8, pp. 1361-1366 (1995).

The International Search Report and the Written Opinion for International Application No. PCT/IB2014/063780 (8 pages).

The Restriction Requirement for U.S. Appl. No. 13/961,421 dated Jan. 2, 2015 (5 pgs.).

The Ex parte Quayle for U.S. Appl. No. 13/961,421 dated Jul. 8, 2015 (28 pgs.).

The Office Action for U.S. Appl. No. 13/961,421 dated Dec. 15, 2015 (10 pgs.).

The Notice of Allowance for U.S. Appl. No. 13/961,421 dated Mar. 25, 2016 (8 pgs.).

* cited by examiner

FEEDTHROUGH WITH INTEGRATED BRAZELESS FERRULE

CROSS-REFERENCE TO RELATED APPLICATION

This application is a divisional of U.S. patent application Ser. No. 13/961,421, entitled "METHOD OF FORMING FEEDTHROUGH WITH INTEGRATED BRAZELESS FERRULE," having a filing date of Aug. 7, 2013, which is incorporated herein by reference.

BACKGROUND

Implantable medical devices, such as cardiac pacemakers or defibrillators, typically include a metal housing having a feedthrough device (often referred to simply as a feedthrough) which establishes electrical connections between a hermetically sealed interior of the metal housing and an exterior of the medical device. Feedthroughs typically include an insulator and a frame-like metal ferrule disposed about a perimeter edge of the insulator. The ferrule is configured to fit into a corresponding opening in the metal housing, with the ferrule typically being welded to the housing to ensure a hermetic seal with respect to the interior of the housing. Electrical conductors or "feedthrough pins" extend through the insulator to provide electrical pathways between the hermetically sealed interior of the housing and an exterior of the medical device. The insulator electrically isolates the feedthrough pins from one another and from the metal ferrule and housing.

The ferrule and insulator are typically joined to one another via a brazing or soldering process. Forming the metal ferrule (typically via a machining process) to meet the tight tolerances required to maintain a desired gap (about 10-50 µm) between the ferrule and insulator that is necessary to achieve a quality braze joint is difficult. Additionally, if the gap is not maintained during the brazing process or if the brazing itself is not properly performed, a weak joint may be formed between the ferrule and the insulator that may lead to premature failure of the implantable device.

For these and other reasons there is a need for the embodiments of the present disclosure.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

It is to be understood that the features of the various exemplary embodiments described herein may be combined with each other, unless specifically noted otherwise.

In accordance with one embodiment of the present disclosure, a method of forming a feedthrough device for an implantable medical device is provided. A bulk insulator having a longitudinal length extending between first and second end faces is provided, the bulk insulator including one or more conducting elements extending therethrough between the first and second end faces, and having a perimeter surface along the longitudinal length. A metal, metal alloy, or cermet is deposited on the perimeter surface to form a ferrule directly on the perimeter surface of the bulk insulator. After the metal, metal alloy, or cermet has been deposited, the bulk insulator is segmented along the longitudinal length into individual segments each having a thickness, with each individual segment forming a feedthrough device.

According to one embodiment, the perimeter surface of the bulk insulator is metallized with a metallization layer prior to depositing the metal, metal alloy, or cermet. In one embodiment, the metallization layer is of a metal selected from a group consisting of titanium, niobium, platinum, palladium, and gold, and has a thickness in a range from 0.2 µm to 10 µm.

Embodiments described herein for depositing a metal, metal alloy, or cermet on the insulator to form a ferrule directly on the perimeter surface thereof provides advantages over known processes. Depositing the metal ferrule directly on the insulator, or on a metallized layer thereon, eliminates braze and solder joints which exist between the ferrule and insulator of conventional ferrules, thereby providing a stronger and more reliable hermetic seal there between. Depositing the ferrule directly on the insulator also eliminates the costly and time consuming process of first machining ferrules to the tight tolerances required to provide a proper gap between the insulator and ferrule necessary to produce quality brazing and solder joints. It also eliminates the necessity of maintaining such gap as required to ensure quality joints during the brazing and soldering process itself, thereby resulting in stronger and more consistent hermetic seals between the ferrule and insulator.

According to one embodiment, the metal, metal alloy, or cermet is deposited using a suitable powder deposition process. In one embodiment, the powder deposition process comprises a Laser Engineered Net Shaping™ process to coat the perimeter surface of the insulator with the metal, metal alloy, or cermet. In one embodiment, the powder deposition process comprises a plasma thermal spraying process to coat the perimeter surface of the insulator. In one embodiment, the metal or metal alloy is deposited with a thickness in a range from 200 μm to 800 μm. In one embodiment, the metal or metal alloy forming the ferrule comprises one of a group consisting of niobium, titanium, titanium alloy, tantalum, tungsten, molybdenum, cobalt, zirconium, chromium, platinum, and alloy combinations thereof. In one embodiment, the cermet comprises a combination of a ceramic, such as aluminum oxide ($Al_2O_3$) and Zirconium dioxide ($ZrO_2$), for example, and a metal, such as Niobium, Molybdenum, titanium, cobalt, zirconium, chromium, platinum, tantalum, and iridium, for example.

In one embodiment, machining is performed after deposition of the metal, metal alloy, or cermet on the perimeter surface of the insulator to provide the ferrule with a desired final cross-sectional shape. In one embodiment, deposition of the metal, metal alloy, or cermet is finely controlled so that the resulting ferrule has a desired final cross-sectional shape. Controlling deposition of the metal, metal alloy, or cermet in this fashion substantially reduces or eliminates the time and expense required to machine conventional ferrules.

According to one embodiment, the insulator comprises aluminum oxide and the conductive elements comprise a cermet. Using cermet conductive elements also eliminates braze and/or solder joints between the conductive elements and the insulator and such that the entire ferrule is brazeless/solderless.

In one embodiment, the insulator is preheated using a laser to a desired temperature within a range from 800 to 1500° C. prior to depositing the metal, metal alloy, or cermet on the perimeter surface. According to one embodiment, the insulator is preheated to the desired temperature in a time period ranging from 15 to 180 seconds. In one embodiment, the laser is used to ramp down a temperature of the insulator after deposition of the metal, metal alloy, or cermet thereon. Controlling the temperature of the insulator in this fashion reduces or eliminates the potential for cracking of the insulator that might otherwise result from a thermal shock during the deposition process.

Another aspect provides a method of forming a feedthrough device for an implantable medical device including providing an insulator having one or more conducting elements extending therethrough, the insulator having a perimeter edge surface, metallizing the perimeter edge surface to provide a metallized layer thereon, and depositing a metal, metal alloy, or cermet having a thickness in a range from 200 to 800 μm on the metallized layer to form a ferrule thereon and thereby form the feedthrough device. According to one embodiment, such method provides depositing the metal, metal alloy, or cermet on individual feedthrough devices in lieu of forming such devices from a bulk insulator.

Such method provides several of the advantages discussed above, including forming stronger and more consistent and uniform hermetic seals between ferrules and insulators relative to conventional solder and braze joints, and the elimination of the formation and maintenance of a high-tolerance gap between the ferrule and insulator which is required for producing convention solder and braze joints.

One embodiment provides a feedthrough for an implantable medical device including a ferrule comprising a metal, metal alloy, or cermet that is configured to be jointed to a case of the implantable device, an insulator substantially surrounded by the ferrule and sharing an interface therewith, the insulator comprising a glass or ceramic material, and conductive elements formed through the insulator providing an electrically conductive path through the insulator. The feedthrough is characterized in that there is no braze, solder, or weld joint at the interface between the ferrule and the insulator and that there is no braze or solder at interfaces between the insulator and the conductive elements. The complete absence of braze or solder joints which characterizes such a feedthrough enables the feedthrough to provide an improved and more durable hermetic seal for an implantable medical device in which it is employed.

Figure 1A:
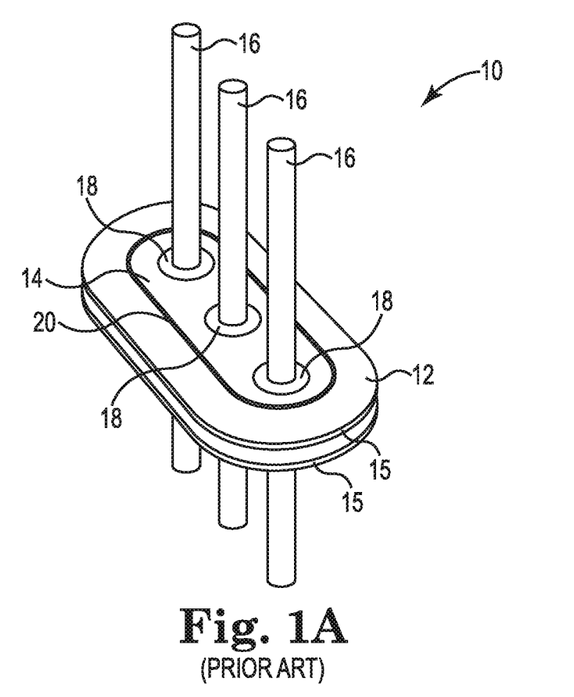
FIGS. 1A and 1B illustrate a feedthrough device in accordance with the prior art.
Figure 1B:
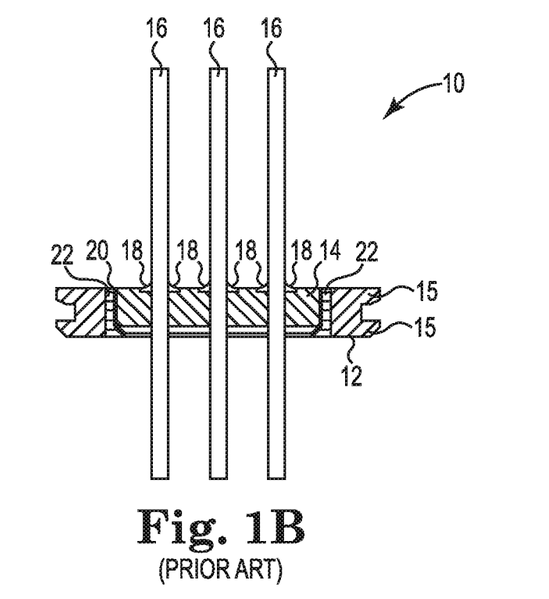

FIGS. 1A and 1B respectively illustrate perspective and sectional views of a conventional feedthrough device 10, such as for an implantable medical device. Feedthrough device 10 includes a ferrule 12, an insulator 14 and feedthrough pins 16. Ferrule 12 is an annular, frame-like metal structure forming an interior opening in which insulator 14 is disposed. Feedthrough pins 16 extend through insulator 14, with insulator 14 serving to electrically insulate feedthrough pins 16 from one another and from ferrule 12.

Ferrule 12 is configured to fit into a corresponding opening of a metal case for an implantable medical device. Typically, ferrule 12 is welded to the metal case so that it is tightly secured thereto and to ensure a hermetic seal with respect to an interior space of the medical device defined by the metal case. Feedthrough pins 16 extending through insulator 14 provide electrical connection from the interior to the exterior of the metal case while maintaining a hermetic seal. Flanges 15 are sometimes provided on ferrule 12 to further aid in securing feedthrough device 10 to the opening of the case of the implantable medical device and ensuring ifs hermetic seal.

Typically, ferrule 12 is a bio-compatible metal, such as titanium or niobium, while insulator 14 is a ceramic or glass material. When coupling insulator 14 to ferrule 12, a perimeter edge of insulator 14 is typically metalized (i.e. a metal coating is applied, such as by sputtering, for example) to provide a thin metal coating 20 thereon, and insulator 14 is placed within the interior opening defined by ferrule 12. A brazing process, using a brazing material 22, such as gold, is then carried to join ferrule 12 to insulator 14 via metal coating 20. Similarly, a braze 18 is often used to couple feedthrough pins 16 to insulator 14.

In order to achieve a quality braze between ferrule 12 and insulator 14, a proper gap needs to be maintained between ferrule 12 and insulator 14, typically about 10-50 μm, so that capillary action will properly draw brazing material 22 into the gap to create a strong and reliable hermetic seal. Forming ferrule 12, typically via machining processes, to meet the tight tolerances required to provide the desired gap between the ferrule 12 and insulator 14, as well as to the dimensions of the opening in the metal case, can be difficult. If the gap between the ferrule 12 and insulator 14 is too small, the brazing material 22 may not be adequately drawn into the gap, resulting in a weak joint. Also, during the brazing process, intermetallics are always formed between the brazing material 22 and ferrule 12, with the intermetallics being brittle as compared to the brazing material 22. If the gap is too small, the amount of intermetallics may be large relative to the amount of brazing material 22, resulting in a brittle joint that can crack and compromise the hermetic seal.

Figure 2A:
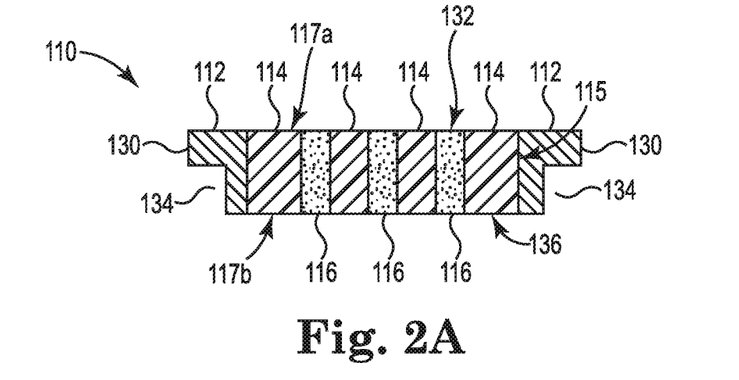
FIG. 2A illustrates a cross-sectional view of a feedthrough assembly in an implantable medical device in accordance with one embodiment.

FIG. 2A is cross-sectional view illustrating a feedthrough device 110 according to one embodiment of the present disclosure. Feedthrough device 110 includes a ferrule 112, an insulator 114, and conducting elements 116, with insulator 114 having a perimeter edge surface or perimeter surface 115 extending between a first or upper major surface 117a and a second or lower major surface 117b. According to embodiments described herein, ferrule 112 is formed from one of a metal, metal alloy, or cermet. Feedthrough device 110 is characterized, relative to conventional feedthrough devices, by the absence of a metallization layer and a braze material (such as metallization layer 20 and braze material 22 of FIG. 1B, for example) between the material of ferrule 112 and the glass or ceramic material of insulator 114. Instead, according to embodiments of the present disclosure, the metal of ferrule 112 is deposited directly on the material of insulator 114 on perimeter 115, using deposition techniques which will be discussed in greater detail below, to form a hermetic seal therebetween without the use of braze or solder.

Ferrule 112 can be formed using the deposition techniques to have a variety of shapes and cross-sections. According to one embodiment, as illustrated by FIG. 2, ferrule 112 is formed with a flange 130 extending laterally along an upper surface 132, resulting in a notch 134 along a lower surface 136, giving ferrule 112 a stepped, rectangular shape in cross-section. According to one embodiment, a desired final shape of ferrule 112 is achieved directly via the deposition process. In one embodiment, machining is performed after initial deposition of the metal of ferrule 112 to achieve the desired final shape of ferrule 112.

According to one embodiment, as illustrated by FIG. 2A, insulator 114 and conducting elements 116 are formed in a first process such that interfaces between insulator 114 and conducting elements 116 are also hermetically sealed without the use of a braze or solder. According to one example of such an embodiment, insulator 114 is a ceramic material, such as aluminum oxide ($Al_2O_3$), and conducting elements 116 are a cermet material.

In the context of one embodiment, the terms, "cermet" or "cermet-containing," refers composite materials made of ceramic materials in a metallic matrix (binding agent). These are characterized by their particularly high hardness and wear resistance. The "cermets" and/or "cermet-containing" substances are cutting materials that are related to hard metals, but contain no tungsten carbide hard metal and are produced by powder metallurgical means. A sintering process for cermets and/or cermet-containing elements is the same as that for homogeneous powders, except that the metal is compacted more strongly at the same pressuring force as compared to the ceramic material. The cermet-containing bearing element has a higher thermal shock and oxidation resistance than sintered hard metals. According to one embodiment, the ceramic components of the cermet are aluminum oxide ($Al_2O_3$) and zirconium dioxide ($ZrO_2$), for example, and niobium, molybdenum, titanium, cobalt, zirconium, chromium, and platinum, for example, may be employed as the metallic components.

According to one embodiment, the ceramic of insulator 114 of FIG. 2A is a multi-layer ceramic sheet into which a plurality of vias is introduced. The cermet of conducting elements 116 is then introduced into the vias. In one embodiment, both materials are introduced in a green state, and the combination is fired together. Accordingly, the joining of the insulator 114 and conducting elements 116 forms a hermetic seal therebetween without the use of braze or solder.

Figure 2B:
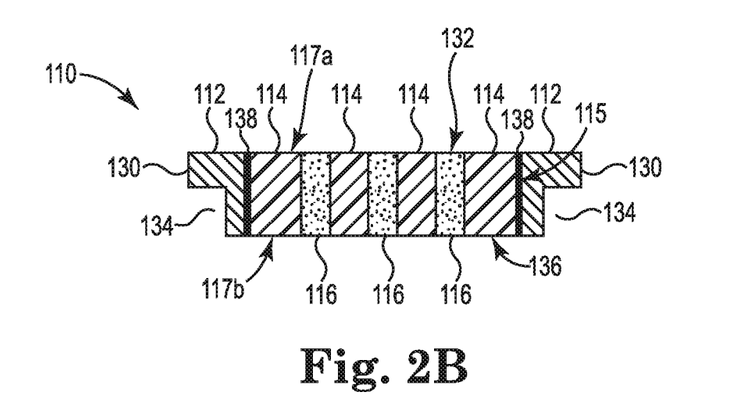
FIG. 2B illustrates a cross-sectional view of a feedthrough assembly in an implantable medical device in accordance with one embodiment.

FIG. 2B is a cross-sectional view of feedthrough device 110 of FIG. 2A, but further includes a metallized layer 138 disposed on the perimeter surface 115 of ceramic insulator 114 at the interface between insulator 114 and the material of ferrule 112. According to one embodiment, metallized layer 138 is disposed on insulator 114 via a sputter coating process. According to one embodiment, metallized layer 138 is disposed on insulator 114 via an electroplating process. According to one embodiment, metallized layer 138 comprises a bio-compatible metal, such as Niobium, Platinum, Palladium, Titanium, and Gold, for example. In one embodiment, metallized layer 138 is deposited so as to have a thickness in a range from 0.2 to 10 µm. As will be described in greater detail below, after deposition of metallized layer 138 on insulator 114, a metal, metal alloy, or cermet is deposited on and built-up on metallized layer 138 to form ferrule 112.

Figure 3:
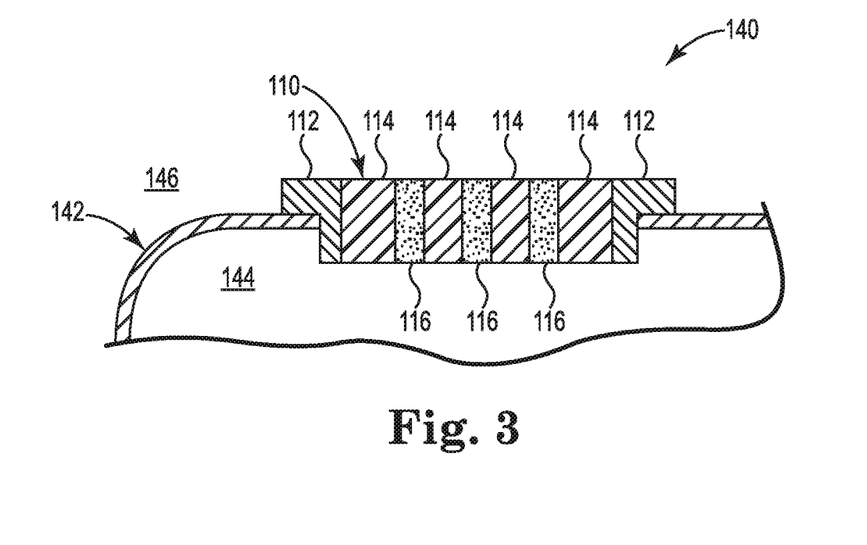
FIGS. 3 illustrates a cross-sectional view of a feedthrough assembly in an implantable medical device in accordance with one embodiment.

FIG. 3 is a cross-sectional view illustrating portions of an implantable medical device 140 having a metal case 142 in which feedthrough device 110 of FIG. 2A is installed. In one embodiment, feedthrough device 110 is positioned within an opening in metal case 142, and ferrule 112 is laser welded to metal case 142 such that an interior 144 of metal case 142 is hermetically sealed relative to its exterior 146.

By forming insulator 114 and conducting elements 116 using a cermet material, as described above, and by depositing the metal of ferrule 112 directly on a perimeter surface of insulator 114, a ferrule formed according to embodiments of the present application, such as ferrule 112 of FIG. 2A, provides hermetic seals between ferrule 112 and insulator 114, and between insulator 114 and conducting elements 116 without the use of braze or solder. As such, a feedthrough device according to the present disclosure, such as feedthrough device 110 of FIG. 2A, eliminates shortcomings associated with the braze and/or solder joints of conventional feedthrough devices (such as illustrated by FIGS. 1A and 1B, for example), and provides a more reliable hermetic seal between an interior and exterior of an implantable device, such as between the interior 144 and exterior 146 of implantable medical device 140.

According to embodiments, a suitable deposition process, including suitable powder deposition processes, is employed to deposit the material forming ferrule 112 (e.g. metal, metal alloy, cermet) directly on insulator 114. Examples of such deposition processes include powder deposition processes such as Laser Engineered Net Shaping™ and plasma thermal spraying, for example.

Figure 4:
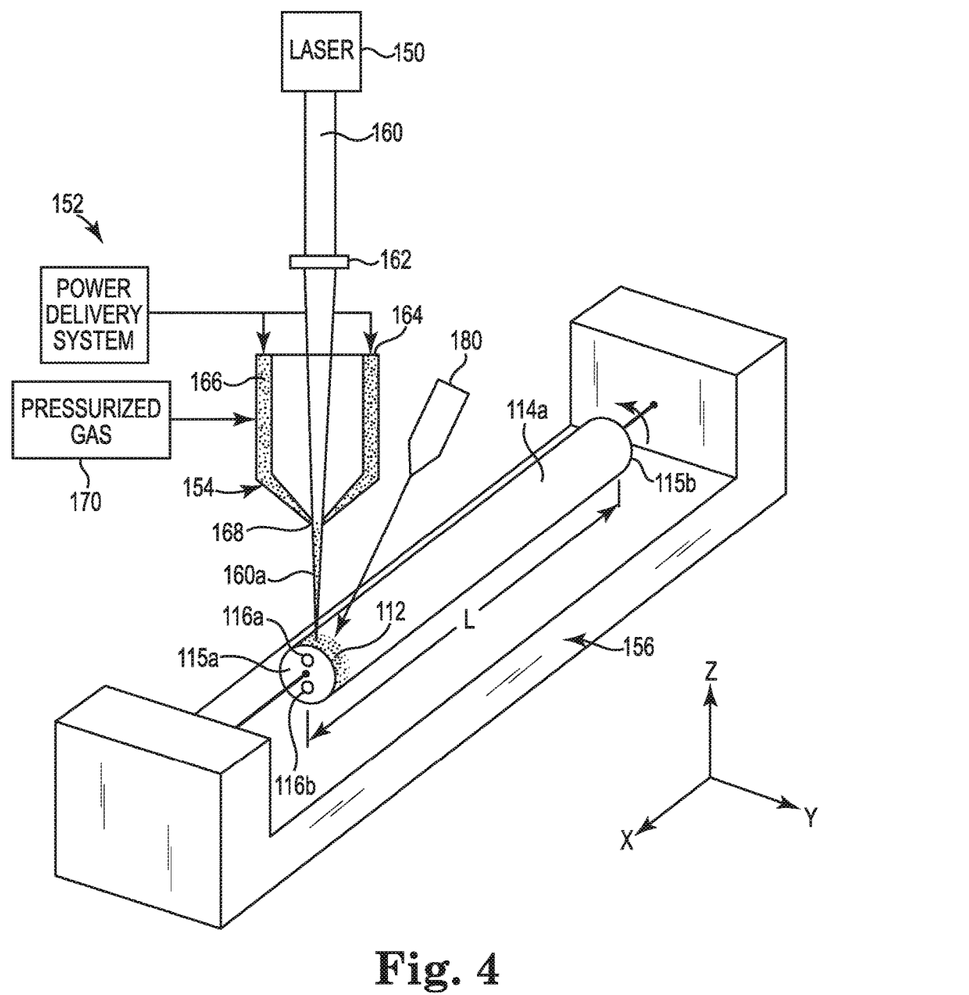
FIG. 4 illustrates a method of forming a feedthrough device in accordance with one embodiment.

FIG. 4 is a block and schematic diagram generally illustrating one embodiment of a Laser Engineered Net Shaping™ (LENS®) process for depositing a metal, metal alloy, or cermet on insulator 114 to form ferrule 112. The LENS process employs a high power laser 150, a powder delivery system 152, a deposition or print head 154, and a translation table 156.

According to one embodiment, a bulk insulator 114a having a length "L" between first and second end surfaces 115a, 115b, and one or more conducive elements extending through insulator 114a from first end surface 115a to a second end surface 115b, such as conductive elements 116a and 116b, is mounted on translation table 156. According to one embodiment, bulk insulator 114a has been previously formed, such as by the cermet process described above, so that conductive elements 116a and 116b comprise cermet and a brazeless/solderless hermetic seal exists between conductive elements 116a and 116b. According to one embodiment, bulk insulator 114 includes a metallization layer 138a disposed on its external circumferential surface, such as via a sputtering process or electroplating process as described above. Although illustrated in FIG. 4 as having a circular cross-section, bulk insulator 114a can have a variety of cross-sectional shapes, such as rectangular or oval, for example.

During the deposition process, laser 150 provides a high power laser beam 160 which travels through the center of deposition head 154 and is focused to a point on the surface of bulk insulator 114a by one or more lenses 162. Powder delivery system 152 provides a fine powder 164 of a metal, metal alloy, or cermet components to a plenum 166 about the circumference of deposition head 154. The fine powder 164 is coaxially injected into the focused high power laser beam 160a at an outlet 168 of deposition head 154. Powder 164 can be circumferentially injected into focused laser beam 160a by gravity or by using a pressurized carrier gas. The powder 164 is sintered by focused laser beam 160a and deposited on the surface of bulk insulator 114a, or onto metallized layer 138a when present, such as illustrated by the exemplary embodiments of FIGS. 2A and 2B.

According to one embodiment, powdered metals used to form ferrule 112 include Ti (Titanium), Ti6Al4V (Titanium Alloy), Nb (Niobium), Ta (Tantalum), W (Tungsten), or alloy combinations of these, for example. According to one embodiment, cermet powder includes a ceramic component, such as Aluminum Oxide (Al2O3) and Zirconium dioxide (ZrO2), for example, and a metal component such as Niobium, Molybdenum, titanium, cobalt, zirconium, chromium, platinum, tantalum, and iridium, for example. According to one embodiment, combinations of these components forms the cermet powder which is laser sintered onto insulator 114a.

According to one embodiment, lasers used for laser 150 include Nd:YAG, Fiber, and CO2, for example. According to one embodiment, Nd:YAG and Fiber are employed due to their approximately 1 μm wavelength having a higher optical absorption into the metals.

As the melted/sintered powder 164 is deposited onto the surface of bulk insulator 114 (or onto metallization layer 138a if present), translation table 156 is controlled so as to rotate bulk insulator 114a about the x-axis and to translate bulk insulator 114a along the x-axis to deposit melted/sintered powder 164 in a desired fashion on the circumferential surface of bulk insulator 114a and thereby form ferrule 112. Melted/sintered powder 164 is deposited in a series of layers to build the deposited metal up to a desired thickness to form ferrule 112. According to one embodiment, translation table 156 also controls movement of bulk insulator 114a along the z-axis as the thickness of the material deposited on bulk insulator 114a increases. In other embodiments, a position of deposition head 154 along the z-axis can be controlled.

According to one embodiment, deposition of the metal, metal alloy, or cermet onto bulk insulator 114a is precisely controlled so that the metal, metal alloy, or cermet is built-up and directly deposited with the desired final shape of ferrule 112, such as the rectangular, stepped shape of ferrule 112 of FIG. 2A, without a need for post-deposition machining. According to one embodiment, the metal, metal alloy, or cermet is deposited on bulk insulator 114 in a range from 200 μm to 800 μm to form ferrule 112. In one embodiment, an inert gas 170 is supplied to deposition head 154 to shield the metal or metal alloy from oxygen, thereby suppressing oxidation of the metal or metal alloy, and so that the metal or metal alloy sinters properly and can be controlled more accurately. According to one embodiment, mechanical machining is performed after the initial deposition of the metal, metal alloy, or cermet on bulk insulator 114a to achieve the desired final shape of ferrule 112.

In one embodiment, an additional laser 180 is used to preheat the material of bulk insulator 114a to reduce the thermal shock from laser 150 during the deposition process and thereby reduce the chance of cracking of the ceramic material of bulk insulator 114a during deposition. According to one embodiment, laser 180 is configured to scan the surface of insulator 114 to raise the temperature of bulk insulator 114a from room temperature to a temperature of 800-1,500° C. In one embodiment, laser 180 is a $CO_2$ laser. According to one embodiment, laser 180 using a ramp rate of 15-180 seconds to heat bulk insulator 114a from room temperature to the desired preheat temperature. According to one embodiment, laser 180 is similarly used to carry out a cool down process to ramp the temperature down to room temperature after deposition of the metal of ferrule 112.

In one embodiment, the preheating of bulk insulator 114a, the deposition of the metal, metal alloy, or cermet onto the surface of bulk insulator 114a to form ferrule 112, and the subsequent cool down process is carried out in a vacuum or in an inert environment (e.g. argon) to keep the metal or metal alloy from being oxidized.

Figure 5:
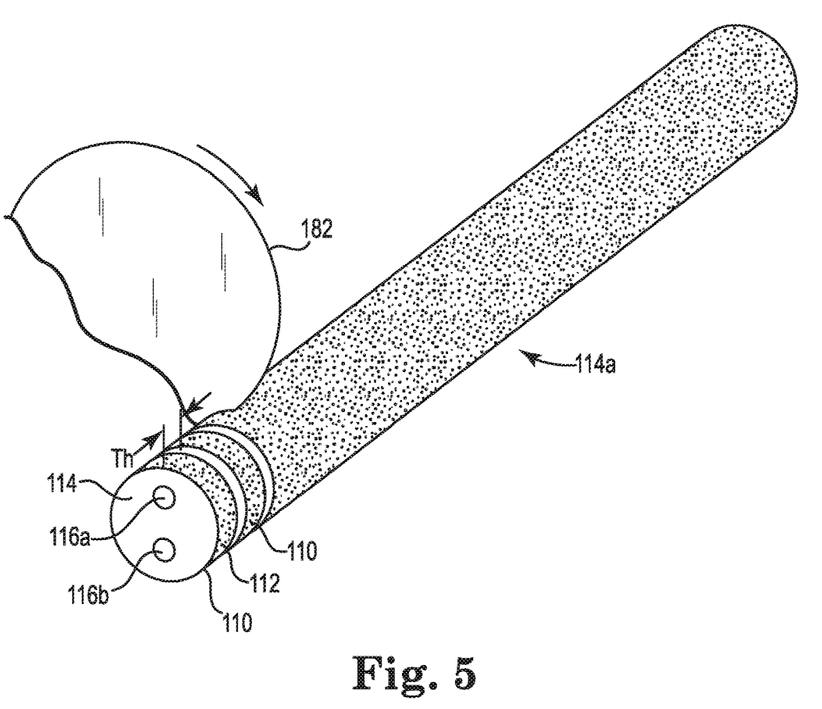
FIG. 5 illustrates a method of segmenting a length of a bulk feedthrough device into a plurality of individual feedthroughs in accordance with one embodiment.

As illustrated by FIG. 5, according to one embodiment, after completing the deposition of the material forming ferrule 112 on the length "L" of bulk insulator 114a to form a resulting length "L" of a bulk feedthrough device 110a, the bulk feedthrough device 110a is cut into segments to form multiple individual feedthrough devices 110 (such as illustrated by FIGS. 2A and 2B), each having a desired thickness "Th". According to one embodiment, the length "L" of bulk feedthrough device 110a is segmented using a saw 182.

In other embodiments, not illustrated herein, in lieu of performing the deposition of the material of ferrule 112 on bulk insulators (such as bulk insulator 114a), individual insulators 114 having one or more conducting elements 116 extending therethrough are coated with the metal, metal alloy, or cermet, such as by the above described process of FIG. 4, to form individual feedthrough devices 110.

Figure 6:
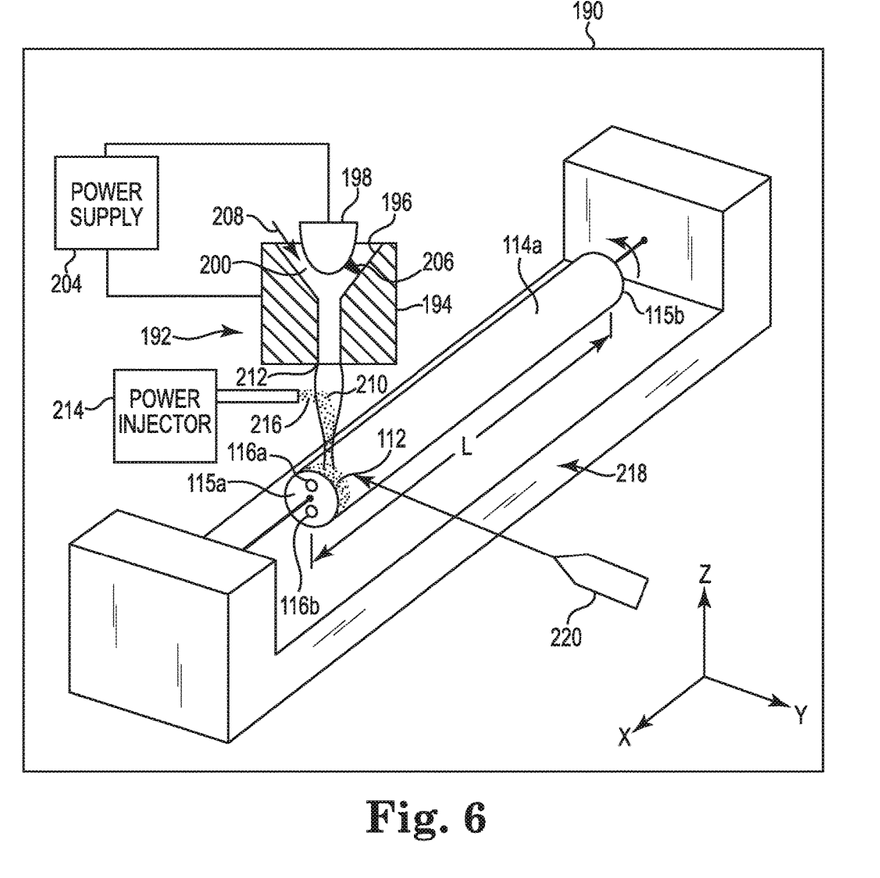
FIG. 6 illustrates a method of forming a feedthrough device in accordance with one embodiment.

FIG. 6 is a block and schematic diagram generally illustrating one embodiment of a process for depositing material directly on bulk insulator 114a (or on individual insulators 114) to form ferrule 112. The process illustrated by FIG. 5 is commonly referred to as plasma thermal spraying, and employs a chamber 190 in which a plasma gun 192 is disposed. Plasma gun 192 includes a body 194 having a conical cavity 196 in which a cathode 198 is disposed and forms an annular cavity 200 there about. A low-pressure, inert gas atmosphere is created within an interior of chamber 190 (e.g. argon, an argon-helium mixture, or an argon-hydrogen mixtures, for example).

During a coating process, a power supply 204 is energized to create an arc 206 between 194 and cathode 198 in annular passage 200. A plasma gas, such as a mixture of argon and helium, for example, is flowed through annular passage 200 and a high temperature, high velocity plasma gas stream 210 is expelled via nozzle 212. A powder injection system 214 injects a fine powder 216 of a metal, metal alloy, or cermet components which is entrained in the plasma gas stream 210, and which are subsequently melted and deposited on the surface of bulk insulator 114a to form ferrule 112. Materials similar to those described above with respect to the LENS process of FIG. 4 may be employed for the metal, metal alloys, and cermet. As also described above with regard to the LENS process of FIG. 4, a translation table 218 rotates bulk insulator 114a about the x-axis and controls lateral movement of bulk insulator 114a along the x-axis so as to deposit the materials forming ferrule 114 in a desired fashion on the outer diameter of the ceramic material of bulk insulator 114a.

Similar to that described above with respect to the LENS process of FIG. 4, according to one embodiment, deposition of the metal, metal alloy, or cermet onto bulk insulator 114a (or onto metallized layer 138 when present) is precisely controlled so that the material is built-up and directly deposited with the desired final shape of ferrule 112, such as the rectangular, stepped shape of ferrule 112 of FIG. 2A, without the need for post-deposition machining. According to one embodiment, the metal, metal alloy, or cermet is deposited on bulk insulator 114a in a range from 200 μm to 800 μm to form ferrule 112. In other embodiments, post-deposition machining is performed to achieve a desired final shape of ferrule 112.

According to one embodiment, a laser 220 is employed to carry out preheating and cool down processes similar to LENS process described above by FIG. 4. Also, as described above by FIG. 5, after deposition of ferrule 112 onto bulk insulator 114a by the plasma thermal spraying process of FIG. 6, the resulting bulk feedthrough device 110a is segmented to individual feedthrough devices 110, such as illustrated by FIGS. 2A and 2B, for example.

Figure 7:
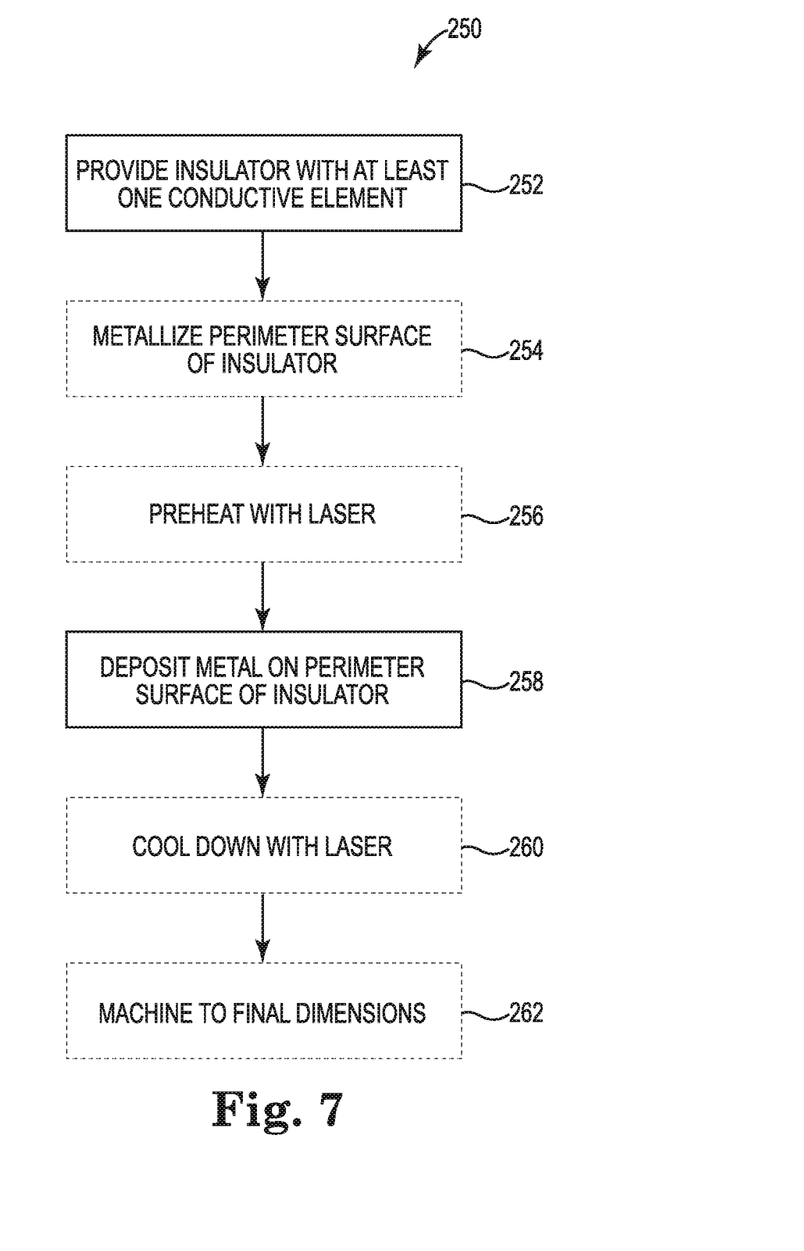
FIG. 7 is a flow diagram illustrating a method of forming a feedthrough assembly in accordance with one embodiment.

FIG. 7 is a flow diagram illustrating a process 250 of forming a feedthrough device in accordance with one embodiment. Process 250 begins at 252 with receiving an insulator having one or more conducting elements extending therethrough. According to one embodiment, the insulator is one such as insulator 114 of FIG. 2A, wherein conducting elements 116 are of a cermet material such that there is no braze or solder at interfaces between conductive elements 116 and the material of insulator 114, such as a glass or ceramic material. According to one embodiment, the insulator is a bulk insulator, such as bulk insulator 114a illustrated by FIG. 4, which has a length "L" between opposing end faces, with cermet conducting elements extending between the opposing faces. According to one embodiment, the insulator has a circular or oval cross-section, for example, but can have any number of cross-sectional shapes.

According to one embodiment, after receiving the insulator, the insulator is optionally metallized to form a metallization layer about an exterior edge surface of the insulator, such as metallization layer 138 about a perimeter edge surface 115 of insulator 114 as illustrated by the embodiment of FIG. 2A.

At 258, a material, such as a metal, metal alloy, or cermet, for example, for forming a ferrule, such as ferrule 112 of the embodiment of feedthrough 110 illustrated by FIG. 2A, is deposited on a perimeter surface of the insulator. According to one embodiment, the material forming ferrule 112 is deposited using a LENS® process, such as generally illustrated and described by FIG. 4. According to one embodiment, the material forming ferrule 112 is deposited using a plasma thermal spraying process, such as generally illustrated and described by FIG. 6. According to one embodiment, the process for deposition of the material forming the ferrule is controlled to the extent that the material is deposited such that the ferrule is directly formed with a desired final shape (e.g. cross-sectional shape). In one embodiment, the material is deposited on individual insulators, such insulator 114 of FIG. 2A. In one embodiment, the material is deposited on the perimeter surface of a bulk insulator, such as bulk insulator 114a of FIG. 4, for example.

Optionally, at 256, according to one embodiment, the perimeter surface of the insulator is preheated with a laser, for example, to a desired temperature prior to the deposition of metal at 258. Preheating the perimeter surface of the insulator, such as with laser 180 of FIG. 4, reduces the thermal shock to insulator 114 that might otherwise be caused by the material deposition process, and thereby reduces cracking of insulator 114 during the deposition process.

According to one embodiment, process 250 ends at 258. However, in one embodiment, process 250 optionally includes, as indicated at 260, performing a controlled cool down of insulator 114 and the deposited (e.g. metal, metal alloy, cermet), such as via laser 180 of FIG. 4. Such a controlled cool down further reduces the chances for thermally induced cracking of the material of insulator 114 and improves the chances of achieving a better bond between the deposited material forming ferrule 112 and the ceramic or glass material, for example, of insulator 114.

Additionally, according to one embodiment, process 250 optionally includes, at 262 a machining process when the material of ferrule 112 is not deposited so as to have a desired final shape. Such machining process machines the "rough" deposition of the material ferrule 112, such as deposited by the processes of FIGS. 4 and 6, for example, to a final desired shape.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of the specific embodiments discussed herein. Therefore, it is intended that this invention be limited only by the claims and the equivalents thereof.

What is claimed is:

1. A feedthrough for a medical implantable device comprising:
    a ferrule comprising a metal that is configured to be welded to a case of the implantable device;
    an insulator substantially surrounded by the ferrule and sharing an interface therewith, the insulator comprising a glass or ceramic material;
    conductive elements formed through the insulator providing an electrically conductive path through the insulator;
    characterized in that there is no braze, solder, or weld joint at the interface between the ferrule and the insulator and that there is no braze or solder at interfaces between the insulator and the conductive elements.

2. The feedthrough of claim 1, wherein the metal forming the ferrule comprises one of a group consisting of niobium, titanium, titanium alloy, tantalum, tungsten, molybdenum, cobalt, zirconium, chromium, platinum, and alloy combinations thereof.

3. The feedthrough of claim 1, wherein the insulator comprises aluminum oxide and the conductive elements comprise a cermet.

4. The feedthrough of claim 1, wherein the ferrule has a thickness in a range from 200 micrometers to 800 micrometers.

5. The feedthrough of claim 1, further comprising a metallized layer at the interface between the ferrule and the insulator.

6. The feedthrough of claim 5, wherein the metallized layer has a thickness in a range from 0.2 micrometers to 10 micrometers.

7. The feedthrough of claim 6, wherein the metallized layer is of a metal comprising one selected from a group consisting of titanium, niobium, platinum, palladium, and gold.

8. A feedthrough for a medical implantable device comprising:
   a ferrule comprising a metal having a thickness in a range from 200 to 800 micrometers that is configured to be welded to a case of the implantable device;
   an insulator substantially surrounded by the ferrule and sharing an interface therewith, the insulator comprising a glass or ceramic material;
   conductive elements formed through the insulator providing an electrically conductive path through the insulator;
   characterized in that there is no braze, solder, or weld joint at the interface between the ferrule and the insulator.

9. The feedthrough of claim 8, wherein the metal forming the ferrule comprises one of a group consisting of niobium, titanium, titanium alloy, tantalum, tungsten, molybdenum, cobalt, zirconium, chromium, platinum, and alloy combinations thereof.

10. The feedthrough of claim 8, wherein the insulator comprises aluminum oxide and the conductive elements comprise a cermet.

11. The feedthrough of claim 8, further characterized in that there is no braze or solder at interfaces between the insulator and the conductive elements.

12. The feedthrough of claim 8, further comprising a metallized layer at the interface between the ferrule and the insulator.

13. The feedthrough of claim 12, wherein the metallized layer has a thickness in a range from 0.2 micrometers to 10 micrometers.

14. The feedthrough of claim 13, wherein the metallized layer is of a metal comprising one selected from a group consisting of titanium, niobium, platinum, palladium, and gold.

* * * * *

UNITED STATES PATENT AND TRADEMARK OFFICE
CERTIFICATE OF CORRECTION

PATENT NO. : 9,814,891 B2
APPLICATION NO. : 15/225321
DATED : November 14, 2017
INVENTOR(S) : Jacob Markham et al.

Page 1 of 1

It is certified that error appears in the above-identified patent and that said Letters Patent is hereby corrected as shown below:

On the Title Page

Column 1, (73) Assignee: delete "HERAEUS DUETSCHLAND GMBH & CO. KG" and insert in place thereof --HERAEUS DEUTSCHLAND GMBH & CO. KG--.

Signed and Sealed this
Eighth Day of January, 2019

Andrei Iancu
*Director of the United States Patent and Trademark Office*